United States Patent [19]

Kojima et al.

[11] Patent Number: 4,747,930
[45] Date of Patent: May 31, 1988

[54] AIR/FUEL RATIO SENSOR

[75] Inventors: Takao Kojima; Hiroyuki Ishiguro; Yoshihide Kami, all of Aichi, Japan

[73] Assignee: NGK Spark Plug Co., Ltd., Japan

[21] Appl. No.: 68,293

[22] Filed: Jul. 1, 1987

[30] Foreign Application Priority Data

Jul. 1, 1986 [JP] Japan ................................ 61-155788

[51] Int. Cl.$^4$ ...................... G01N 27/12; G01N 27/58
[52] U.S. Cl. ..................................... 204/412; 204/425; 338/34
[58] Field of Search ................ 204/425, 412, 410, 1 S; 338/34

[56] References Cited

U.S. PATENT DOCUMENTS 4,578,172 3/1986 Yamada et al. ..................... 204/412
4,594,139 6/1986 Asayama et al. ................... 204/410

Primary Examiner—G. L. Kaplan
Attorney, Agent, or Firm—Sughrue, Mion, Zinn, Macpeak, and Seas

[57] ABSTRACT

An air-fuel ratio sensor including a box member having a wall made of oxygen ion-conductive electrolyte having a pair of porous electrodes on opposite sides and a diffusion-limiting portion providing communication between the inside and outside of the box member, and an oxygen gas sensing element formed within the box member by injection and firing. The oxygen gas sensing element has a resistance which varies in accordance with the oxygen partial pressure of the atmosphere in which the sensor is immersed.

6 Claims, 3 Drawing Sheets

AIR/FUEL RATIO SENSOR

BACKGROUND OF THE INVENTION

The present invention relates to an A/F (air-fuel) ratio sensor used for detecting the A/F ratio of an air/fuel mixture supplied to a combustor such as an internal combustion engine. More particularly, the present invention relates to an A/F ratio sensor that employs an oxygen pump element composed of an oxygen ion-conductive solid electrolyte and an oxygen gas sensing element composed of an electron-conductive semiconductor metal oxide.

With a view to improving fuel economy and reducing emissions while providing improved operability, it has been proposed that feed-back control be performed on combustors, such as internal combustion engines, so as to attain a desired A/F ratio according to specific operating conditions. Numerous A/F ratio sensors have been proposed for use in such feedback control.

For example, according to the system shown in Unexamined Published Japanese Patent Application No. 190652/1984, an oxygen concentration electrochemical cell element employing atmospheric air as a reference oxygen source and an oxygen pump element using atmospheric air as an oxygen supply source are placed in a face-to-face relationship with an enclosed compartment formed therebetween. The compartment communicates with the ambient atmosphere by way of a diffusion-limiting portion. The oxygen pump element is controlled so that the oxygen partial pressure in the enclosed compartment is held constant, with the electric current (pump current) that flows through the pump element being used to indicate the A/F ratio of the sensed atmosphere over the full operating range of the combustor, including both the fuel-lean region and fuel-rich region.

Another A/F ratio sensor system is described in Unexamined Published Japanese Patent Application No. 153155/1983. In this system, an oxygen concentration electrochemical cell element which contacts the sensed atmosphere on one side and an enclosed compartment on the other side and an oxygen pump element which also contacts the sensed atmosphere on one side and the enclosed compartment on the other side are placed in a face-to-face relationship with the enclosed compartment being formed therebetween. The compartment communicates with the sensed atmosphere by way of a diffusion-limiting portion. The oxygen pump element is controlled so that the oxygen partial pressure in the enclosed compartment is held constant, with the pump current being used to indicate the A/F ratio of the ambient atmosphere over the full operating range including both the fuel-lean region and the fuel-rich region.

The first type of A/F ratio sensor described above requires a channel for introducing atmospheric air, hence cannot be sealed completely, and may be adversely affected during service by foreign matter such as moisture. The second type of A/F ratio sensor mentioned above does not require the introduction of atmospheric air, but its output characteristics are ambiguous in that one output value is associated with two different values of A/F ratio, specifically, values in both the fuel-lean and fuel-rich regions. In order to ensure a nonambiguous, one-to-one correspondence between the output value and sensed A/F ratio over the full operating range including both the fuel-rich and fuel-lean regions, an additional sensor is required to indicate whether the combustor is operating in the fuel-rich region ($\lambda < 1$) or fuel-lean region ($\lambda > 1$).

This problem may be overcome by an A/F ratio sensor in which an oxygen gas sensing element that employs an electron-conductive semiconductor metal oxide such as $TiO_2$ and which does not require a reference source is combined with an oxygen pump element composed of an oxygen ion-conductive solid electrolyte. However, an oxygen gas sensing element made of an electron-conductive semiconductor metal oxide such as $TiO_2$ and an oxygen pump element made of a $ZrO_2$-based solid solution compound are difficult to produce simultaneously by conventional techniques since they require different temperatures and atmospheres for firing. On the other hand, if the two elements are fired separately and joined together afterward, it is very difficult to attain a perfectly fitting unitary assembly.

SUMMARY OF THE INVENTION

The latter problem is solved by the A/F ratio sensor of the present invention which comprises a box member, at least a portion of whose wall is made of an oxygen ion-conductive electrolyte having a pair of porous electrodes on opposite sides thereof. The box member also has a diffusion-limiting portion that establishes communication between the inside and outside thereof. An oxygen gas sensing element formed within the box member by means of injection and firing provides a varying resistance in accordance with the oxygen partial pressure of the sensed atmosphere.

The oxygen ion-conductive solid electrolye of which the box member is made is typically a solid solution compound of zirconia and yttria or calcia. Other usable materials include solid solution compounds of cerium dioxide, thorium dioxide and hafnium dioxide, a solid solution compound of a perovskite type oxide, and a solid solution compound of a trivalent metal oxide. Of these solid solution compounds, those based on zirconia are most preferred because of their ready availability. The porous electrodes on the solid electrolyte may be formed by various methods with platinum, gold or other such materials. In one method, a power of a suitable material, selected from the above-listed metals and which is used as the principal component, is worked into paste and the paste is printed in a predetermined pattern on the solid electrolyte by a thick-film deposition technique, followed by sintering of the printed coat. In another method, a powder of the starting material is applied onto the solid electrolyte by a suitable thin-film deposition technique such as flame spraying, chemical plating or evaporation.

The diffusion-limiting portion in the box member may be formed by various methods, such as by forming holes or slits that establish communication between the inside and outside of the box member, or by replacing part of a wall of the box member with a porous material. Holes are particularly preferable since they provide for easy injection and firing of the material of the oxygen gas sensing element.

The box member may be in the form of a cylinder with both ends closed, or in the form of a closed rectilinear box. In the former case, the box member is formed entirely of a solid electrolyte. In the latter case, one rectangular plate of a solid electrolyte having a pair of electrodes formed thereon is overlaid in sequence with a spacer having a rectangular opening (which is later filled with the oxygen gas sensing element) and another rectangular plate, and the three members are compressed together and fired to form the desired box member.

The oxygen gas sensing element may be formed of an oxide of a transition metal element selected from among those having atomic numbers of 21 (Sc) to 30 (Zn), 39 (Y) to 48 (Cd), 57 (La) to 80 (Hg), and 89 (Ac) to 103 (Lr). Oxides of these transition metal elements have a tendency to form nonstoichiometric compounds wherein the ratio of elemental metal to oxygen is a nonintegral value. Due to this nonstoichiometricity, the electrical conductivity of these oxides strongly varies in accordance with the oxygen partial pressure of the sensed atmosphere. Similar effects are attained whether these oxides are used independently or in combination. Particularly preferable oxides are $SnO_2$, $TiO_2$, $Nb_2O_5$, $V_2O_5$, $CrO_3$, $CoO$ and $NiO$ because their electrical conductivities are highly sensitive to variations in oxygen partial pressure and because they have high durability. Yet higher durability can be achieved by mixing these oxides, for instance, $CoO$, with a non-transition metal oxide such as $MgO$.

The A/F ratio sensor of the present invention can be produced by a method wherein one or more of the oxides mentioned above is injected into a previously made box member and fired in situ. More specifically, a paste of the oxides is injected under pressure into the box member through holes serving as the diffusion-limiting portion, and subsequently fired. Alternatively, the paste may be injected through holes other than those serving as the diffusion-limiting portion (which holes are closed at a later stage) and subsequently fired. In order to ensure higher stability in the face of varying temperatures, a heat generating element is preferably provided in the box member or the oxygen gas sensing element. Part of the heat generating element may be joined to one of the electrodes on the oxygen gas sensing element so that electrical power applied to the heating element can also be used for operation of the oxygen gas sensing element. This arrangement provides a particular advantage in that the measuring circuit for oxygen gas detection can be simplified.

An A/F ratio sensor of the present invention having the above-described construction is operated as follows:

The solid electrolyte of which the box member is formed and the pair of electrodes formed thereon serves as an oxygen pump element. Depending upon the polarity of the voltage applied between the electrodes, the oxygen pump element will pump oxygen into or out of the box portion. The oxygen gas sensing element is designed so that its resistance varies with the oxygen partial pressure of the sensed atmosphere. When the sensed atmosphere changes from the fuel-lean to fuel-rich region or vice versa, the resistance of the oxygen gas sensing element will change by about three to four orders of magnitude at the transition from one region to the other.

When the air/fuel mixture is in the fuel lean region, the electrode on the outside of the oxygen pump element (i.e., the outside of the box member) is supplied with a positive voltage, while a negative voltage is applied to the electrode on the inside of the pump element. As a result, oxygen ions are caused to migrate through the solid electrolyte in the pump element to move from the inner electrode to the outer electrode, whereby oxygen gas from inside the box member is pumped to the outside of the oxygen pump element.

When oxygen gas has been pumped out of the box member, a difference is produced between the oxygen partial pressure in the box member and that of the gas being sensed by the action of the diffusion-limiting portion in the box member. The oxygen partial pressure in the box member is measured as the electrical resistance of the oxygen gas sensing element. If the amount of current (pump current) flowing through the pump element is adjusted in such a way that the measured resistance is maintained at a predetermined constant level, a substantially linear relationship is attained between the pump current (which is proportional to the differential partial pressure as described above) and the content of oxygen in the gas being analyzed, thereby enabling determination of the oxygen level of that gas.

When the air/fuel mixture is in the fuel-rich region, the oxygen partial pressure in the box member will be low, even if the oxygen pump element is not actuated in such a way as to reduce the oxygen partial pressure. Therefore, in order to maintain the resistance of the oxygen gas sensing element at a constant value, the direction of the pump current flowing through the oxygen pump element should be reversed. Stated more specifically, if the air/fuel mixture is in the fuel-rich region, the oxygen in the box member will be partially consumed by unburnt hydrocarbons and carbon monoxide in the exhaust gas, and hence the oxygen partial pressure in the box member will be sufficiently low that the resistance of the oxygen gas sensing element will drop below the predetermined level. Therefore, in order to maintain the resistance of the oxygen gas sensing element at the predetermined value, oxygen must be pumped into the gas diffusion portion by operating the oxygen pump element. To this end, the pump current is caused to flow in the direction opposite to that when the air/fuel mixture is in the fuel-lean region. The value of the required pump current is proportional to the amounts of unburnt hydrocarbons and carbon monoxide in the exhaust gas.

However, since the outer electrode of the oxygen pump element is exposed to the sensed atmosphere, the oxygen pump element does not have much oxygen available in the fuel-rich region and the linear relationship between pump current and A/F ratio applies only for A/F values of up to about 10. If it is necessary to effect A/F ratio measurement beyond this point in the fuel-rich region, atmospheric air is introduced to make contact with the outer electrode of the oxygen pump element to ensure that it has a sufficient amount of oxygen available for correct A/F ratio measurement.

Therefore, whether the air/fuel mixture is in the fuel-lean or fuel-rich region, a linear relationship is maintained between the pump current and the A/F ratio by controlling the former in such a way that the output of the oxygen gas sensing element of the A/F ratio sensor is maintained at a predetermined constant level. Alternatively, the A/F ratio may be determined from the resistance of the oxygen gas sensing element with the pump current held constant.

As described above, A/F ratio sensor of the present invention is composed of a box member and an oxygen gas sensing element formed in the box member by means of injecting and firing a suitable oxide material. The oxygen pump element provided by the box member and the encased oxygen gas sensing element are integrated into a perfectly unitary assembly. This means that the atmosphere around the oxygen gas sensing element is always the same as the atmosphere around the oxygen pump element and that there will be minimum delay in A/F ratio detection, even if fluctuations occur in the atmosphere inside of the box member.

DESCRIPTION OF THE PREFERRED EMBODIMENTS

Figure 1:
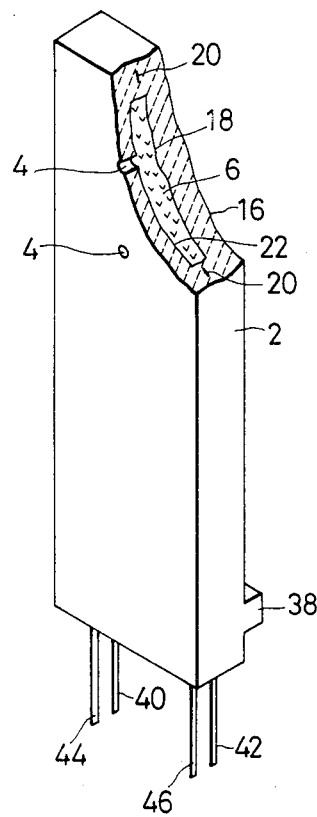
FIG. 1 is a partial cut-away view of an A/F ratio sensor constructed according to a preferred embodiment of the present invention.

A preferred embodiment of an A/F ratio sensor of the present invention is hereunder described with reference to FIGS. 1 and 2, which are a partial cutaway view and an exploded view, respectively.

The A/F ratio sensor of this embodiment includes a box member 2 and an oxygen gas sensing element 6 formed by injecting a suitable oxide material into the box member through diffusion limiting holes 4 and firing the same in situ.

Figure 2:
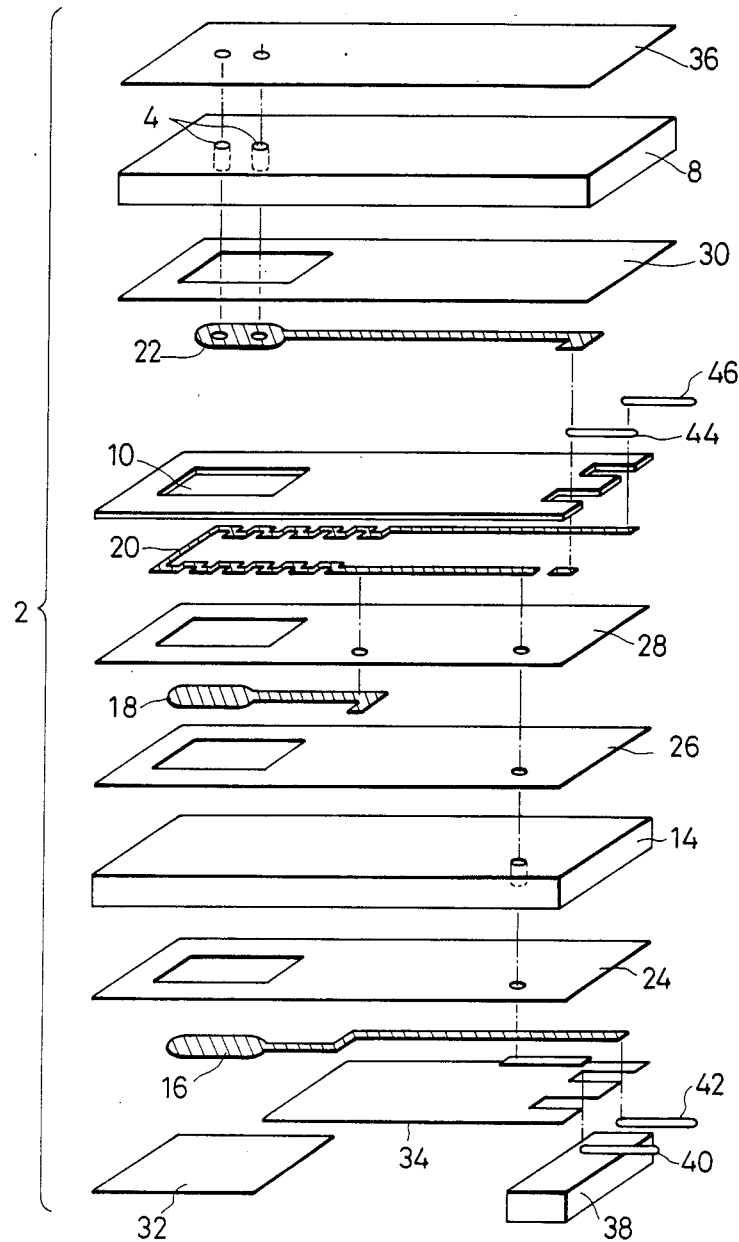
FIG. 2 is an exploded view of the sensor of FIG. 1.

With reference to FIG. 2, the box portion 2 is formed by stacking a box forming member 8, a spacer 12, and a solid electrolyte plate 14. The box forming member 8, which has two diffusion limiting holes 4, measures 38.5 mm long, 5 mm wide and 0.7 mm thick. The spacer 12 measures 38.5 mm long, 5 mm wide and 80 microns thick, and has an opening 10 (2 mm long and 5 mm wide) which is to be filled with the oxide gas sensing element 6. The solid electrolyte plate 14 which serves as an oxygen pump element measures 38.5 mm long, 5 mm wide and 0.7 mm thick. Both the box forming member 8 and the solid electrolyte plate 14 are made of a $ZrO_2$-$Y_2O_3$ solid solution compound, and the spacer 12 is formed of $Al_2O_3$. The box forming member 8 need not be made of a $ZrO_2$-$Y_2O_3$ solid solution compound and may be formed of another suitable heat-resistant material such as $Al_2O_3$.

The solid electrolyte plate 14 is provided with a pair of electrodes 16 and 18 and a heat generating element 20. The box forming member 8 is provided with one electrode 22 for the oxygen gas sensing element 6. The other electrode for the element 6 is in the form of an electrode 18 on the solid electrolyte plate 14. Accordingly, the electrode 18 serves not only as the other electrode for the oxygen gas sensing element 6, but also as one of the two electrodes for the oxygen pump element.

An insulating $Al_2O_3$ layer 24 is provided between electrode 16 and the solid electrolyte plate 14, another insulating $Al_2O_3$ layer 26 is provided between the solid electrolyte plate 14 and the electrode 18, and a third insulating $Al_2O_3$ layer 28 is provided between the electrode 18 and the heating element 20. An insulating $Al_2O_3$ layer 30 is also disposed between the electrode 22 and the box forming member 8. The electrode 16 is provided with protective $Al_2O_3$ layers 32 and 34, and the box forming member 8 is also provided with a protective $Al_2O_3$ layer 36. The underside of the solid electrolyte plate 14 is provided with a fastening device 38 with which the A/F ratio sensor of the embodiment under discussion can be mounted on a metal fixture (not shown).

The electrodes 16, 18, 22 and heating element 20 are connected to leads 40, 42, 44 and 46 via through-holes or other suitable arrangement, as indicated by broken lines in FIG. 2. The electrode 18 is connected to the heating element 20 at about halfway along the length of the element 20 via a through-hole so that power applied to the element 20 can be used for driving the oxygen gas sensing element 6. If a voltage of 14 volts is applied to the heating element 20 which is connected to the electrode 18 at the point shown in FIG. 2, a voltage of about 1 volt is supplied to the oxygen gas sensing element 6.

The A/F ratio sensor of the embodiment being discussed can be produced by the following procedure:

First, a mixture of 94 mol % $ZrO_2$ and 6 mol % $Y_2O_3$ is wet-ground for 45 hours to form a uniform blend. The blend is dried and then calcined at 1,380° C. for 2 hours. The calcined product is wet-ground for 45 hours to obtain particles at least 80% of which have a size of about 2.5 microns or less.

The resulting $ZrO_2$-$Y_2O_3$ particles are mixed with solvents (e.g., methylethylketone and toluene) and binders (e.g., polyvinyl butyral and dibutyl phthalate), and the mixture is defoamed under vacuum to make a slurry, which is then worked into green sheets of the box forming member 8 and the solid electrolyte plate 14.

In the next step, a 2:1 mixture of platinum black and platinum sponge is mixed with a binder (Ethocel ™) and solvents (butyl Carbitol ™ and xylene) to make a platinum paste.

Using this platinum paste, electrodes and a heating element are formed on the green sheets in predetermined patterns (see FIG. 2) by a thick-film printing technique. At the same time, a spacer 12, insulation layers 24, 26, 28, 30, and protective layers 32, 34 and 36 are formed by thick-film printing of separately prepared alumina pastes in the patterns shown in FIG. 2. The spacer 12 is formed of three coatings with a thickness of 30 microns that are applied by a thick-film printing process. Each of the insulating layers 24, 26, 28 and 30 is formed by two coatings with a thickness of 15 microns that are applied by thick-film printing. The protective layer 36 is formed by three coatings with a thickness of 15 microns that are applied by thick-film printing. Each of the protective layers 32 and 34 is formed of two coatings with a thickness of 15 microns and one coating with a thickness of 30 microns, all applied by thick-film printing.

Subsequently, the two green sheets are compressed together, heated at 300° C. for 10 hours to remove the resinous component, and fired at 1,520° C. for 4 hours to make a box 2.

A $TiO_2$ paste from which the oxygen gas sensing element 6 is formed is prepared by the following procedures:

A $TiO_2$ powder is mixed with about 7 mol % chloroplatinic acid. After drying at 200° C., the mix is calcined at 1,300° C. for 2 hours in a nitrogen atmosphere. The calcined product is ground in acetone for 40 hours to obtain particles at least 80% of which have a size of no less than 2.5 microns. To the particles, 2 mol % platinum black, 40 wt % methylethylketone, and 20 wt % toluene and added, and the respective components are mixed together for 8 hours. To the resulting mixture are added binders (2.5% polyvinylbutyral and 1.5% dibutylphthalate) and a solvent (40% butyl Carbitol ™), and the resulting mix is worked into a $TiO_2$ paste.

The $TiO_2$ paste is injected under pressure into one of the two diffusion-limiting holes 4 in the box 2 until it reaches the peripheral edge of the other hole 4. The injected paste is dried and fired at 1,200° C. for 1 hour in atmospheric air to obtain the A/F ratio sensor of the embodiment being discussed.

Figure 3:
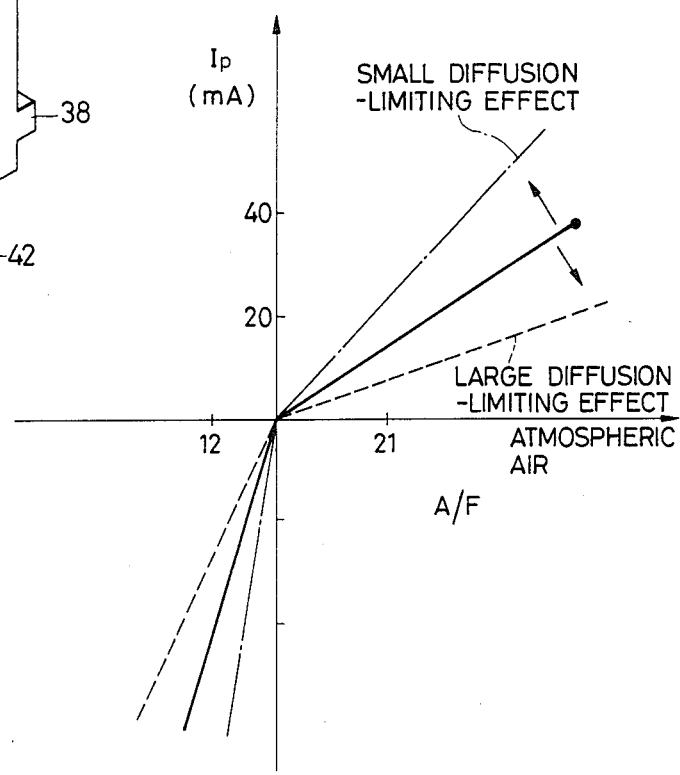
FIG. 3 is a graph showing the operating characteristics of the sensor.

FIG. 3 is a graph showing the operating characteristics of the A/F ratio sensor of the present invention. In the graph, the characteristics of the sensor produced in accordance with the embodiment described above are indicated by the solid line. The characteristics shown in FIG. 3 are expressed in terms of the relationship between the A/F ratio of the atmosphere being sensed and the pump current $I_P$ (the current flowing between the leads 40 and 42) for the case where the oxygen gas sensing element 6 is controlled to produce a constant output.

As is clear from FIG. 3, the A/F ratio sensor of the embodiment under discussion is capable of A/F ratio measurement over a broad operating range, including both the fuel-rich region and the fuel-lean region and extending to atmospheric air. It will be readily appreciated by those skilled in the art that the gradient of the $I_P$ vs. A/F ratio profile will be changed if the diffusion-limiting effect of the holes 4 is modified by changing their number and/or diameter. If the diffusion-limiting effect of the holes 4 is increased, the slope of the $I_P$ vs. A/F ratio profile becomes less steep (as indicated by a dashed line), and it becomes more steep in the opposite case (as indicated by a broken line).

The oxygen gas sensing element 6 of the A/F ratio sensor of the embodiment under discussion is formed by injecting a $TiO_2$ paste into the preliminarily constructed box 2 and firing the same in situ. Therefore, the element 6 is completely integral with the oxygen pump element, which is part of the box 2. The sensor has a very good response to variations in A/F ratio and is capable of carrying out A/F ratio detection more rapidly than prior art systems. In addition, the inventive A/F ratio sensor can be manufactured easily and with a very high yield.

The A/F ratio sensor of the present invention is composed of a box member formed preliminarily and an oxygen gas sensing element formed by injecting a suitable oxide material into the box member and firing the same in situ. With this arrangement, the oxygen gas sensing element and the oxygen pump element forming part of the box member provide a perfectly unitary assembly which ensures good response to variations in A/F ratio of the sensed atmosphere. As a further advantage, the sensor of the present invention can be manufactured easily and with a high yield, thereby contributing to the conservation of resources.

Using the A/F ratio sensor of the present invention, A/F ratio control of an internal combustion engine can be accomplished over a broad operating range including both the fuel-lean and fuel-rich regions. An additional advantages is that the sensor does not require a reference oxygen source and can be operated with a simple construction. Due to the absence of a reference oxygen source, the sensor provides a more reliable performance since there can be no fluctuations due to variations in the oxygen partial pressure of the reference oxygen source.

What is claimed is:

1. An air/fuel ratio sensor comprising:
   a box member having a wall made of an oxygen ion-conductive electrolyte having a pair of porous electrodes on opposite sides thereof, said box member also having a diffusion-limiting portion establishing communication between an inside and an outside of said box member; and
   an oxygen gas sensing element formed within said box member by injection of a material forming said oxygen gas sensing element into said box member and subsequent firing of said material, said oxygen gas sensing element having a resistance which varies in accordance with an oxygen partial pressure of an atmosphere in which said sensor is immersed.

2. The air/fuel ratio sensor according to claim 1, wherein said material forming said oxygen gas sensing element is injected through said diffusion-limiting portion, which is in the form of a hole, and by subsequent firing in situ.

3. The air/fuel ratio sensor according to claim 1, wherein at least one of said electrodes for said oxygen gas sensing element is an inner electrode formed on an inside surface of said solid electrolyte.

4. The air/fuel ratio sensor according to claim 1, further comprising a heat generating element for heating said oxygen gas sensing element.

5. The air/fuel ratio sensor according to claim 1, wherein said solid electrolyte is a zirconia-based solid solution compound.

6. The air/fuel ratio sensor according to claim 1, wherein said material forming said oxygen gas sensing element comprises at least one compound selected from the group consisting of $SnO_2$, $TiO_2$, $Nb_2O_5$, $V_2O_5$, $Cr_2O_3$, $CoO$ and $NiO$.

* * * * *